(12) United States Patent
Eilers et al.

(10) Patent No.: US 9,125,772 B2
(45) Date of Patent: Sep. 8, 2015

(54) SANITARY OR INCONTINENCE PAD (75) Inventors: Jörg Eilers, Ulm (DE); Rüdiger Kesselmeier, Herbrechtingen (DE); Andreas Böhmler, Heidenheim (DE); Karina Schwarz, Kammeltal-Reid (DE); Thurid Manns, Heidenheim (DE)

(73) Assignee: PAUL HARTMANN AKTIENGESELLSCHAFT, Heidenheim (DE)

( * ) Notice: Subject to any disclaimer, the term of this patent is extended or adjusted under 35 U.S.C. 154(b) by 222 days.

(21) Appl. No.: 13/641,364

(22) PCT Filed: Mar. 25, 2011

(86) PCT No.: PCT/EP2011/054601
§ 371 (c)(1),
(2), (4) Date: Oct. 15, 2012

(87) PCT Pub. No.: WO2011/128198
PCT Pub. Date: Oct. 20, 2011

(65) Prior Publication Data
US 2013/0041338 A1  Feb. 14, 2013

(30) Foreign Application Priority Data
Apr. 16, 2010  (DE) .......................... 10 2010 015 559

(51) Int. Cl.
*A61F 13/472* (2006.01)
*A61F 13/476* (2006.01)

(52) U.S. Cl.
CPC ............. *A61F 13/472* (2013.01); *A61F 13/476* (2013.01)

(58) Field of Classification Search
CPC .............. A61F 13/476; A61F 13/5616; A61F 2013/586
USPC ........... 604/385.02, 385.201, 385.03–385.05, 604/386, 387, 389, 390
See application file for complete search history.

(56) References Cited

U.S. PATENT DOCUMENTS 5,545,157 A * 8/1996 Van Iten .................... 604/385.04
5,558,657 A   9/1996 Hammons et al.
6,447,495 B1 * 9/2002 Luizzi et al. ............. 604/385.05
(Continued)

FOREIGN PATENT DOCUMENTS

DE    200 09 610     2/2001
EP    0 511 905 A1  11/1992
(Continued)

*Primary Examiner* — Lynne Anderson
*Assistant Examiner* — Kathryn E Ditmer
(74) *Attorney, Agent, or Firm* — Henry M. Feiereisen LLC (57) ABSTRACT

A sanitary or incontinence pad includes a primary pad part extending in a longitudinal direction of the pad, wherein a front end region of the pad covers at least one quarter of an overall longitudinal extension of the pad, and a rear end region of the pad covers at most one quarter of the overall longitudinal extension of the pad, an absorption body for bodily fluids received by the primary pad part, and front and rear wing pairs, each formed by two wings which extend transversely from respective longitudinal sides of the primary pad part, wherein the front wing pair is arranged outside the front end region, and wherein at least 90% of a top-view-surface of the wings of the rear wing pair is arranged within the rear end region, and wherein each wing is foldable about a web of an undergarment and is delimited by front and rear side flanks.

23 Claims, 4 Drawing Sheets (56) References Cited

U.S. PATENT DOCUMENTS

| | | |
|---|---|---|
| 7,056,311 B2 | 6/2006 | Kinoshita et al. |
| 2003/0004484 A1* | 1/2003 | Hammons et al. ....... 604/385.04 |
| 2004/0068244 A1 | 4/2004 | Salone et al. |
| 2006/0217678 A1* | 9/2006 | Ikegami et al. ............... 604/386 |
| 2008/0015536 A1 | 1/2008 | Digiacomantonio et al. |
| 2009/0088719 A1 | 4/2009 | Driskell |
| 2010/0256585 A1 | 10/2010 | Konawa |

FOREIGN PATENT DOCUMENTS

| | | | |
|---|---|---|---|
| EP | 0 731 681 B1 | | 8/2000 |
| JP | 2002330992 A | * | 11/2002 |
| JP | 2006340978 A | * | 12/2006 |
| WO | WO 96/38110 | | 12/1996 |
| WO | WO 98/06367 | | 2/1998 |
| WO | WO 2004105667 A1 | * | 12/2004 |
| WO | WO 2009/041517 | | 4/2009 |

* cited by examiner

SANITARY OR INCONTINENCE PAD

CROSS-REFERENCES TO RELATED APPLICATIONS

This application is the U.S. National Stage of International Application No. PCT/EP2011/054601, filed Mar. 25, 2011, which designated the United States and has been published as International Publication No. WO 2011/128198 and which claims the priority of German Patent Application, Serial No. 10 2010 0015 559.4, filed Apr. 16, 2010, pursuant to 35 U.S.C. 119(a)-(d).

BACKGROUND OF THE INVENTION

The invention relates to a sanitary or incontinence pad with wings which can be folded about the web of an undergarment, wherein the pad has a longitudinal direction and a transverse direction and a front end region in the longitudinal direction which end region covers at least one quarter of the overall longitudinal extension of the pad, and a rear end region in the longitudinal direction which covers at most one quarter of the overall longitudinal extension of the pad, with a primary pad part which extends in the longitudinal direction with its longer dimension and accommodates an absorption body for bodily fluids, and with two wings on each longitudinal side of the primary pad part which project in transverse direction from the primary pad part so as to form a front and a rear wing pair, wherein the front wing pair is arranged outside of the front end region in longitudinal direction so that the front end region is not flanked by wings, wherein the wings of the front wing pair and the rear wing pair are each delimited by a front side flank and a rear side flank.

Sanitary or incontinence pads with wings have been described repeatedly, in particular in WO 96/38110 A1, EP 0 731 681 B1, DE 2000 96 10 U1, WO 98/06367 A1, EP 0 511 905 B1. Proceeding from the genus-forming sanitary or incontinence pad according to WO 96/38110 A1, the present invention is based on the objective to improve the handling of the sanitary article during arrangement on an undergarment and to also optimize the wearing properties of the sanitary article. This poses conflicts of objectives in several regards. On one hand a secure arrangement of the pad on the crotch web of an undergarment is sought to be achieved via an areal extension and configuration of the wings which is as great as possible. However, because of the three dimensionally arched shape of the pad during use it was recognized with the present invention that an expansive wing configuration is also associated with disadvantages, by disadvantageously stiffening the wings, which proves disadvantageous when arranging the pad in the undergarment as well as when wearing the pad. Within the context of the present invention this was found to also be the case when the rear wing pair is not folded about the lateral borders of the leg opening of the undergarment on its outside, but lies flat against the undergarment from the inside, preferably adhesively fixed. In this case the three dimensional deformation of the sanitary article has also disadvantageous effects on the wear comfort of the sanitary article during use.

SUMMARY OF THE INVENTION

The applicant has already recognized this conflict of goals in an inventive manner and in order to avoid the problems described before, proposes to configure a sanitary or incontinence pad of the generic type in such a manner that at least 90% of the top-view-surface of the rear wing pair is arranged within the rear end region. Top-view-surface of the wings relates to the surface area of the wings which is arranged in transverse direction outside of a tangent to the narrowest point of the pad which tangent extends in longitudinal direction between the front and the rear wing pair in the even, spread out state of the pad. For the purpose of determining this area of the wing a straight line which is parallel to the central longitudinal center axis (longitudinal direction) of the sanitary or incontinence pad is placed on both sides, wherein the narrowest point of the pad between the front and rear wing pair is selected as contact point.

Due to the fact that the wings of the rear wing pair are provided substantially completely in the rear end region of the pad with their areal extension, the previously described stiffening resistance which occurs in case of three dimensional bending and is due to the rear wing pair, is smaller because the rear wings are arranged so as to be restricted to a shorter region of the pad in longitudinal direction. In the sanitary or incontinence pad according to the invention the rear wings are thus also not provided directly in the crotch region, which leads to less material in the crotch region. In this respect it is advantageous in a further embodiment of the invention when the rear end region covers at most one fifth ($\frac{1}{5}$) in particular at most one sixth ($\frac{1}{6}$) of the overall longitudinal extension of the pad (front border edge to rear border edge in longitudinal direction, see FIG. 1). The front end region of the pad covers preferably at most one third ($\frac{1}{3}$) in particular at most two sevenths ($\frac{2}{7}$) of the overall longitudinal extension of the pad (front border edge to rear border edge in longitudinal direction 16).

Further, it is advantageous when the wings of the front wing pair are also arranged over or extend over a longitudinal section of the pad which is restricted in longitudinal direction. Preferably, the wings of the front wing pair are arranged with at least 90% of their top-view-surface within a longitudinal section of the pad of at most one quarter ($\frac{1}{4}$) of its overall longitudinal extension. Extending on this thought, it is advantageous when the mentioned longitudinal section adjoins the front end region, wherein the front end region in longitudinal direction covers at most one third ($\frac{1}{3}$), in particular two sevenths ($\frac{2}{7}$) of the overall longitudinal extension of the pad. In particular the mentioned longitudinal section can cover the second quarter of the overall longitudinal extension of the pad (viewed from the front). A wingless longitudinal section between the rear end region of the rear wing pair and the longitudinal section of the front wing pair preferably has a longitudinal extension of at least two twelfths ($\frac{2}{12}$) preferably of at least one quarter ($\frac{1}{4}$) of the overall longitudinal extension of the pad.

It is further advantageous when the extension of the wing of the front and/or rear wing pair in transverse direction over the narrowest point of the pad between the front and the rear wing pair is 20-70 mm, in particular 20-50 mm, in particular 25-45 mm.

It is further advantageous when the top-view-surface of each wing of the rear wing pair each covers a portion of 3-7%, further preferably of 4-6% with regard to the overall area of the sanitary or incontinence pad. The surface portion of the rear wing which is small compared to the overall surface enables an extension which is sufficient in particular for fastening the wing on the inside of the undergarment while avoiding stiffening resistances due to material accumulation in longitudinal direction of the pad.

It is particularly advantageous when the top-view-surface of each wing of the front wing pair covers a portion of 3-7%, further preferably of 4-6% with regard to the overall surface of the sanitary or incontinence pad.

It is further advantageous when the top-view-surface of each wing of the front wing pair is respectively 10-17 cm$^2$, further preferably 11-16 cm$^2$, further preferably 12-15 cm$^2$ further preferably 13-14 cm$^2$ and/or the top-view-surface of each wing of the rear wing pair is respectively 10-17 cm$^2$, further preferably 11-16 cm$^2$, further preferably 12-15 cm$^2$ further preferably 13-14 cm$^2$.

In a preferred embodiment, the overall longitudinal extension of the sanitary or incontinence pad along the longitudinal direction is 150 to 400 mm, in particular 200 to 350 mm, in particular 250 to 300 mm, in particular 275 to 290 mm. In order to realize a configuration and arrangement of the wings which is as compact as possible in a limited rather short longitudinal section of the pad, while nevertheless being able to use an area of the wings which is as large as possible for fastening to the undergarment, it is advantageous when the front side and the rear side flanks of the wings or the front and/or rear wing pair extend with the predominant portion of their track at an angle ($\alpha$, $\beta$)>50° in particular >60°, in particular >65° to the longitudinal direction, wherein the angle is further in particular 60-85°, in particular 60-75°. Here, this relates to the smaller of the two cutting angles between the flank direction and the longitudinal direction. In such an embodiment, the wings are tapered outwardly in transverse direction, wherein their extension may well be steep which allows great wing areas at comparatively moderate wing extensions in longitudinal direction.

Figure 1:
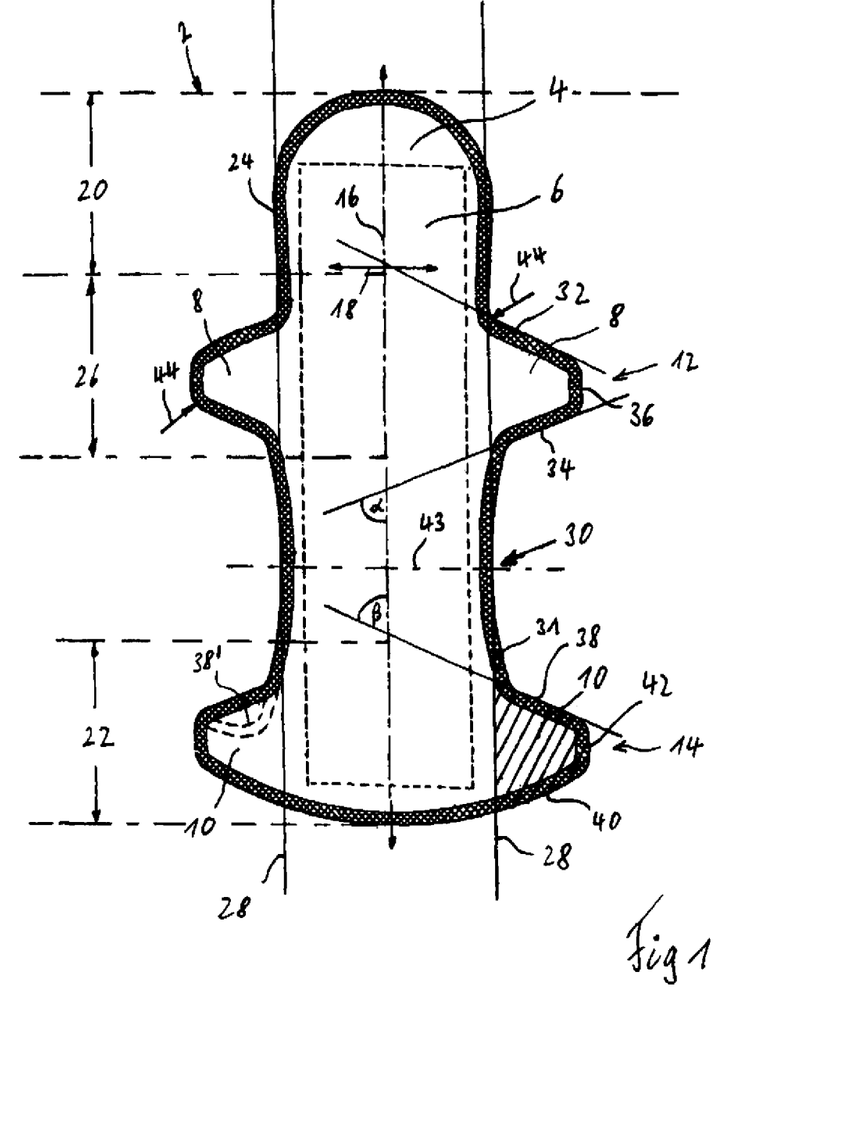
FIG. 1 a sanitary or incontinence pad in the flat spread out state.

In a further embodiment which in FIG. 1 is only outlined in the rear left the front side flanks of the wing of the rear wing pair can extend at an angle >80°, in particular >90°, in particular 90-110°, in particular 90-100° relative to the longitudinal direction. Thus, the length of the connection of the wing to the primary pad part can be extremely shortened in the wings of the rear wing pair, which facilitates their foldability, which however, on the other hand leads to a reduction of the top-view-surface of the wings, which in particular in turn can be compensated by a greater transverse extension.

With regard to the contouring of the wings, the respective front side flanks may for example transition rounded into the rear side flanks. It is also conceivable to provide a flank section between the front side and the rear side flank of a respective wing which flank section is shorter relative to these flanks and which in particular extends substantially in longitudinal direction and into which the flanks transition rounded.

It is conceivable that in the transition between a longitudinal border of the primary pad part and a front side flank or rear side flank of the wings a discontinuous contour is provided, which allows predetermining the formation of a bending or folding line. However, it is advantageous when the outer contour of the pad is configured rounded. Extending on this thought it is advantageous when a curvature radius in the transition between a longitudinal border which substantially extends in the longitudinal direction and the front side flank and/or between the front side flank and the center shorter flank section and/or between the center shorter flank section and the rear side flank and/or between the rear side flank and the longitudinal border of the primary pad part which longitudinal border extends substantially in the longitudinal direction of a respective wing, is 5-12 mm in particular 5-10 mm, in particular 6-9 mm.

According to a further inventive idea which can be advantageous with regard to esthetics it is proposed to configure the wing contours so that the rear flanks of the front wing pair and the front side flanks of the rear wing pair extend straight with the predominant portion of their track. It can further be advantageous when the front side flanks of the rear wing pair extend arch-shaped, preferably by forming a contour which is bulged outward, wherein in this case preferably only a very slight arch-shaped curvature with a curvature radius in the range of 100 mm and more, in particular with a curvature radius of 120-180 mm, further in particular of 140-160 mm further in particular of 150-155 is provided.

Advantageously, the front side flanks of the front wing pair and the rear side flanks of the rear wing pair extend arched.

The curvature of the front side flanks of the front wing pair and/or the rear side flanks of the rear wing pair advantageously contributes to the ergonomic fit of the incontinence or sanitary pad in operating condition. In the operating condition of the folding of the wings of the front wing pair about the crotch web onto the outside of the undergarment and the connection of the wings of the rear wing pair against the inside of the undergarment the curvature of the flanks of the wings supports the flexible adjustment to the three dimensional shape of the pad. Although the front side flanks of the front wing pair and/or the rear side flanks of the rear wing pair are not straight but preferably extend slightly curved arch shaped a tangent can nevertheless be placed to the contour which tangent forms an angle with the longitudinal direction of >5°, in particular >60°, in particular >65° relative to the longitudinal direction, wherein the angle is further in particular 60-85°, in particular 60-75°.

In a particularly advantageous embodiment of the sanitary or incontinence pad, the front side flanks of the front wing pair and the rear side flanks of the rear wing pair are contoured to correspond to one another, so that when folding the pad about an axis which extends in transverse direction (i.e., perpendicular to the longitudinal axis) they can be aligned congruently onto one another. Extending on this inventive idea it is advantageous when the front side flanks of the front wing pair and the rear side flanks of the rear wing pair each follow a circular path or an ellipse or oval shape, whose greater main axis coincides with the aforementioned axis which extends in transverse direction.

It is advantageous when the wings of the rear wing pair at the same time form the rear end of the sanitary or incontinence pad. Here it is advantageous when the rear side flanks of the rear wing pair extend inward toward one another in ergonomic extension of their track and in this way delimit the rear end region of the primary pad part, so that the primary pad part does not have a further extending extension in the rearward direction of the pad.

The wings of the sanitary or incontinence pad have preferably bonding zones for fastening to the undergarment. The bonding zones are provided on the underside of the wings. It is further advantageous when the area of the respective bonding zone per wing is matched to the top-view-surface of the wing. The bonding zone for each wing has preferably an area of 20-50%, further preferably of 20-40% relative to the top-view-surface of the wing. The bonding zone is advantageously arranged centered between the front side and the rear side flank of the respective wing.

The short extension in longitudinal direction, in particular of the rear wing pair, is also advantageous when fastening the pad by means of the bonding zones, because large areal extensions of the wings require a larger portion of bonding zones to avoid folding of material, which in turn would disadvantageously lead to a stiffening resistance in these regions.

Further advantageously, the primary part of the sanitary or incontinence pad is provided with further adhesive zones on the bottom side, i.e., on the side which faces the undergarment during use. These further adhesive zones can be arranged in any desired manner in particular in the form of multiple strips which extend in longitudinal direction of the primary pad part.

The sanitary or incontinence pads can be provided by the manufacturer to the end user in a flat spread out state, in particular in stack form. However, it is also conceivable that a pad is folded about one or multiple folding axes which extend in transverse direction, thereby significantly reducing their longitudinal extension prior to use. Independent of such a folding of the pad about one or multiple transverse axes, the front and/or rear wings can be folded onto the topside or the bottom side of the primary pad part by the manufacturer in order to reduce the transverse extension of the product during storage, sale and delivery to the end user. A longitudinal folding line which is provided for this purpose extends typically in longitudinal direction of the pad and can also include border regions of the primary pad part outside of the actual wings. However, such a longitudinal folding line which is implemented by the manufacturer extends outside of the absorption body of the pad. It can be advantageous when the wings of the front and/or the rear wing pair are folded onto a body-facing top side of the pad by the manufacturer and possibly overlap one another, and when a bonding zone in the respective wings per wing pair which bonding zone is then facing upwards is covered by a single detachable flat, protective element, in particular on paper or foil basis, in particular including anti-stick agents, which protective element covers both wings.

The wings of the front and rear wing pair are preferably composed of a cover sheet material which forms the topside of the sanitary or incontinence pad and a backsheet material which forms the bottom side of the sanitary or incontinence pad. The wings are preferably free of absorption material which is arranged between the cover and back sheet material.

The absorption body extends preferably within the primary pad part and is in particular configured rectangular and introduced in longitudinal direction of the pad. It is also conceivable that the shape of the absorption body in the end regions is adjusted to the contour in the end regions of the primary pad part.

BRIEF DESCRIPTION OF THE DRAWING

For all previously described features, protection is claimed in any combination. Further features, details and advantages of the invention result from the included patent claims and from the drawing and the following description of a preferred embodiment of the sanitary or incontinence pad according to the invention. In the drawing it is shown in:

DETAILED DESCRIPTION OF PREFERRED EMBODIMENTS

FIG. 1 shows a sanitary or incontinence pad overall designated with the reference sign 2 with a primary pad part 4, which includes an absorption body 6 which is rectangular in an exemplary shown case, and with two wings 8 and 10 on each side. The front wings form a front wing pair 12 and the rear wings form a rear wing pair 14.

A longitudinal direction is designated with the reference sign 16 and a transverse direction of the sanitary or incontinence pad which is perpendicular to the longitudinal direction is designated with the reference sign 18. Further, a front end region 20 and a rear end region 22 is indicated in FIG. 1. The longitudinal extension of the front end region 20 covers at least ¼ of the overall longitudinal extension of the sanitary or incontinence pad which in the exemplary shown case is between 275-290 mm. In this front end region 20 no wings are present, but rather the primary pad part 4 delimits the pad with its longitudinal borders 24 which extend substantially in longitudinal direction. Adjoining this front end region 20 is a longitudinal section 26 which for example covers at most ¼ of the overall longitudinal extension of the sanitary or incontinence pad and within which the wings 8 of the front wing pair 12 are arranged with substantially their entire areal extension. In the rear end region 22 the wings 10 of the rear wing pair 14 are arranged. The longitudinal extension of the rear end region 22 is at most ¼, in particular ⅕ of the overall longitudinal extension of the sanitary or incontinence pad.

For delimiting the wings 8, 10 from the primary pad part, a parallel straight line or tangent is placed on each side to the narrowest point 30 of the pad between the front and the rear wing pair 12, 14. Those regions of the pad in transverse direction 18 outside of this straight line or tangent 28, including a sealing border 31 of the pad which in is provided in the exemplary shown case and is several millimeters broad, are assigned to the wings 8, 10. They also contribute to the overall area or top-view-surface of the wings 8, 10 in the sense of the present invention, wherein the narrowest point 30 when in doubt separates the front and rear wings 8, 10 from one another.

The wings 8 of the front side wing pair 12 are delimited by the front side flanks 32 and rear side flanks 34, and by a shorter flank section which lies between the front side and the rear side flanks, and which extends substantially in longitudinal direction 16. The wings 10 of the rear wing pair 14 are also delimited by a front side flank 38 and a rear side flank 40 and a center shorter flank section 42.

The flanks 34, 38 of the front wings 8 or the rear wings 10 which flanks 34, 38 face each other extend substantially straight and intersect the longitudinal direction 16 at an angle α or β which is preferably >65° and in particular between 60° and 85°. Although the flanks 32 and 40 of the front wings 8 or the rear wings 10 which are facing away from one another do not extend straight but rather slightly curved arch shaped, a tangent can nevertheless be placed to the contour (shown in the front) which tangent encloses an angle with the longitudinal direction in the corresponding range 60 to 85. In this way wings 8, 10 which extend relatively short in the longitudinal direction 16 are formed which have a very good handling when fastening to an undergarment and provide a high wearing comfort.

Figure 3:
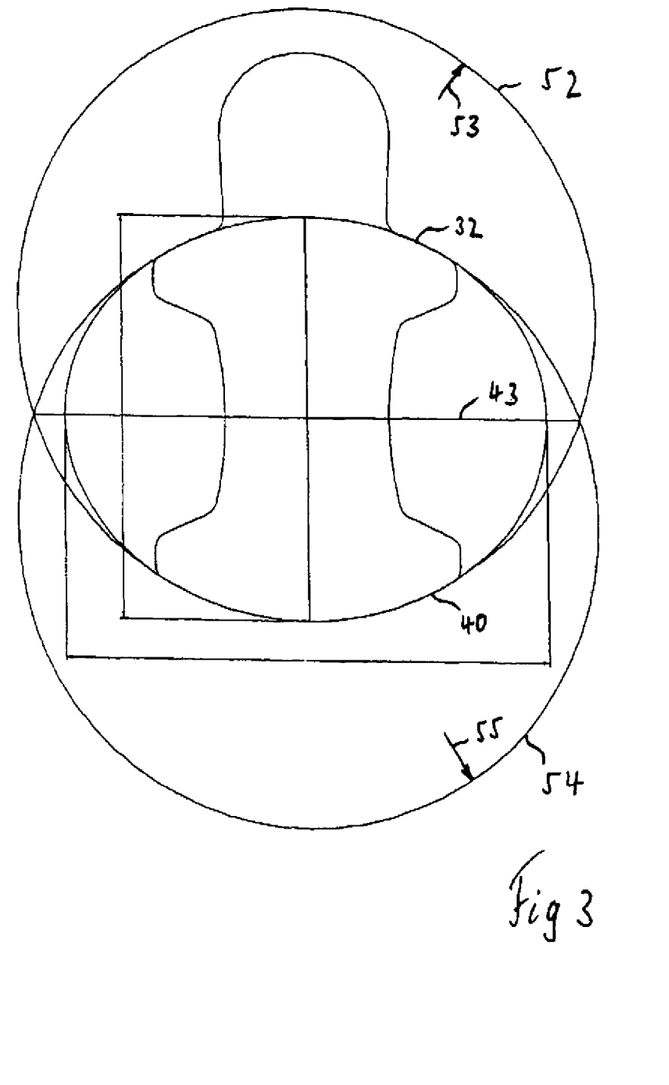
FIG. 3 the sanitary or incontinence pad according to FIG. 1 in the flat unfolded state with schematically indicated extension of the front side flanks of the front wing pair and the rear side flanks of the rear wing pair and FIG. 4 a schematic view of the sanitary or incontinence pad according to FIG. 1 in during use introduced in an undergarment.

The contours of the front side flanks 32 of the front wing pair 12 and the contours of the rear side flanks of the rear wing pair 14 correspond to one another. When the pad is folded onto itself about an axis which extends in a transverse direction, the extension of the front side flanks 32 of the front wing pair and of the rear side flanks 40 of the rear wing pair coincide. In addition, in the exemplary shown case the front side flanks 32 of the front wing pair 12 and the rear side flanks of the rear wing pair follow roughly an oval shape or a roughly elliptical shape, whose greater main axis corresponds to the aforementioned axis 43. This extension of the front side flanks 32 of the front wing pair 12 and the rear side flanks 40 of the rear wing pair 14 is schematically shown in FIG. 3. The flanks 32 or 40 extend arched, their arch shaped curvature can also be roughly described by circles 52 or 54 with a radius 53 or 55, which can be for example 150-155 mm.

The top-view-surface is indicated by hatching by way of example of the right wing 10 of the rear wing pair 14 in FIG. 1. The top-view-surface of a wing 8 of the front wing pair 12 is also 13-14 cm$^2$.

The respective transitions from the longitudinal borders 24 of the primary pad part to the front flank 32 and further to the shorter center flank section 36 and further to the rear side flank and further to the longitudinal borders 24 of the primary pad part and correspondingly in the wings of the rear wing pair 14 are rounded as exemplary shown in FIG. 1. The curvature radius 44 is respectively between 5 and 12 mm.

Figure 2:
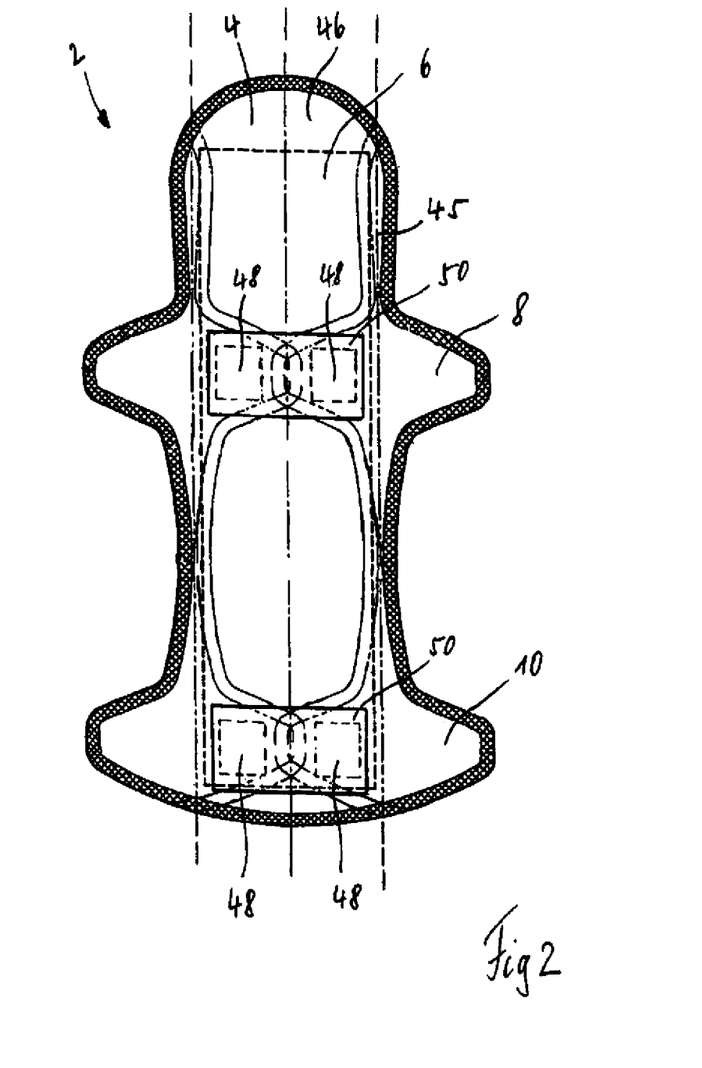
FIG. 2 the sanitary or incontinence pad according to FIG. 1 with indicated folding of the wings carried out by the manufacturer.

FIG. 2 shows the sanitary or incontinence pad 2 according to FIG. 1 and further indicates a folded state provided by the manufacturer in which the wings 8, 10 are folded onto a body facing topside 46 of the primary pad part about a fold line 45 which extends in longitudinal direction 16. In this folded state the outer ends of the wings which are free in transverse direction slightly overlap one another in the region of the longitudinal axis of the pad. Further, bonding zones 48 can be recognized which can be formed by adhesive strips or partial adhesive coatings, but generally also by mechanically acting closing components. This adhesive zone 48 has an area of 20-40% of the top-view-surface of a respective wing. These adhesive zones 48 are covered for each wing pair 12, 14 by a single detachable flat protective element 50, in particular in form of a paper which is coated with anti stick material, which protective element 50 fixes the wings 8, 10 in the folded configuration.

It can be further seen that the folding line 45 provided by the manufacturer extends slightly in transverse direction 18 outside of the absorption body 6 of the pad 2. When using the sanitary or incontinence pad, this folding line typically does not coincide with the folding of the wings 8, 10 about the web of an undergarment. Depending on the size of the web region of the undergarment, the wings 10 of the rear wing pair 14 are also folded about the web of the undergarment after removing the protective element 50, or they are laid against the inside of the undergarment in the buttock area and are preferably adhesively fixed.

Figure 4:
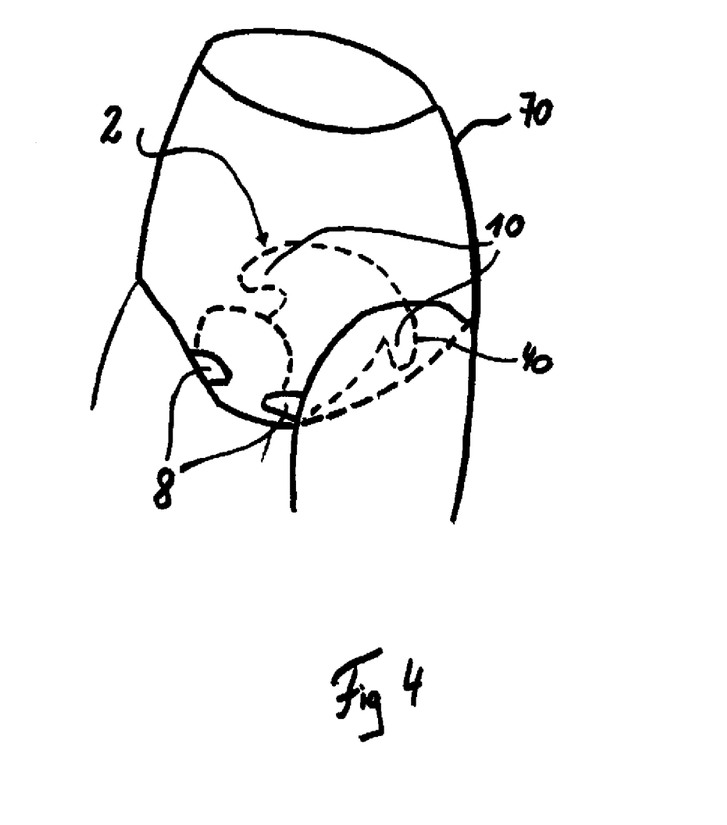

FIG. 4 schematically shows the inside of pad 2 which was introduced into the inside of the undergarment 70 during use, with wings 8 of the front wing pair, which are folded about the web of the undergarment onto the outside of the undergarment and with wings 10 of the rear wing pair which rest against the inside of the undergarment. The short extension of the rear wings 10 in longitudinal direction of the pad enables a greater flexibility of the rear wings within the undergarment. The curvature of the rear side flank 40 of the rear wing 10 supports the ergonomic fit of the pad 2.

What is claimed is:

1. A sanitary or incontinence pad, having a longitudinal and a transverse direction, and a front end region in the longitudinal direction which covers at least one quarter of an overall longitudinal extension of the sanitary or incontinence pad, and a rear end region in the longitudinal direction which covers at most one fifth of the overall longitudinal extension of the sanitary or incontinence pad, said sanitary or incontinence pad comprising:
   a primary pad part extending in the longitudinal direction; and having an absorption body for absorbing bodily fluids;
   two wings extending in the transverse direction from respective longitudinal sides of the primary pad part so as to form a front wing pair, said front wing pair being arranged outside the front end region so that the front end region is not flanked by wings, wherein at least 90% of a top-view-surface of the two wings of the front wing pair is arranged within a subsection of the overall longitudinal extension of the sanitary or incontinence pad, said subsection covering at most one quarter of the overall longitudinal extension of the sanitary or incontinence pad; and
   another two wings extending in the transverse direction from the respective longitudinal sides of the primary pad part so as to form a rear wing pair, wherein at least 90% of a top-view-surface of the another two wings of the rear wing pair is arranged within the rear end region, and wherein the two wings and the another two wings are foldable about a web of an undergarment and are each delimited by a front side flank and a rear side flank, wherein the subsection adjoins the front end region, and wherein the front end region covers at most one third-of the overall longitudinal extension of the sanitary or incontinence pad.

2. The sanitary or incontinence pad of claim 1, wherein the two wings of the front wing pair and/or the another two wings of the rear wing pair extend further than a narrowest point of the sanitary or incontinence pad between the front and rear wing pairs in the transverse direction by 20-70 mm.

3. The sanitary or incontinence pad of claim 1, wherein a top-view-surface of each of the another two wings of the rear wing pair and/or a top-view-surface of each of the two wings of the front wing pair each occupies a portion of 3-7% relative to an overall surface of the sanitary or incontinence pad.

4. The sanitary or incontinence pad of claim 1, wherein a top-view-surface of each of the two wings of the front wing pair is 10-17 cm$^2$, and/or the top view surface of each of the another two wings of the rear wing pair is 10-17 cm$^2$.

5. The sanitary or incontinence pad of claim 1, wherein a predominant portion of each of the front side flanks and rear side flanks encloses on an inside of the respective wings of the front wing pair and/or the rear wing pair an angle of >50° and up to 85°, with the overall longitudinal direction of the sanitary or incontinence pad.

6. The sanitary or incontinence pad of claim 1 wherein respective flank sections between the front side flank and the rear side flank of each of the two wings and each of the another two wings are shorter than the front and the rear side flanks and extend substantially in the longitudinal direction, and wherein the front side flanks and the rear side flanks transition roundedly into the respective flank sections.

7. The sanitary or incontinence pad of claim 6, wherein a curvature radius in a transition between a longitudinal border of the primary part of the pad, which extends substantially in the longitudinal direction, and the front side flank and/or between the front side flank and the flank section and/or between the flank section and the rear side flank and/or between the rear side flank and the longitudinal border of the primary part of the pad, of a respective wing is 5-12 mm.

8. The sanitary or incontinence pad of claim 1, wherein a predominant portion of the rear side flank of each of the two wings of the front wing pair and a predominant portion of the front side flank of each of the another two wings of the rear wing pair extend in a straight line.

9. The sanitary or incontinence pad of claim 1, wherein the front side flank of each of the two wings of the front wing pair and the rear side flank of each of the another two wings of the rear wing pair extend curved in the shape of an arch.

10. The sanitary or incontinence pad of claim 1, wherein the front side flank of each of the two wings of the front wing pair and the rear side flank of each of the another two wings of the rear wing pair are contoured so as to correspond to one another, thereby enabling alignment of the front-and rear side flanks with one another when folding the sanitary or incontinence pad about an axis which extends in the transverse direction.

11. The sanitary or incontinence pad of claim 1, wherein the front side flank of each of the two wings of the front wing pair and the rear side flank of each of the another two wings of the rear wing pair extend along a circular path or an ellipsis or an oval shape, whose greater main axis coincides with an axis which extends in the transverse direction.

12. A sanitary or incontinence pad, having a longitudinal and a transverse direction, and a front end region in the longitudinal direction which covers at least one quarter of an overall longitudinal extension of the sanitary or incontinence pad, and a rear end region in the longitudinal direction which covers at most one fifth of the overall longitudinal extension of the sanitary or incontinence pad, said sanitary or incontinence pad comprising:
    a primary pad part extending in the longitudinal direction; and having
    an absorption body for absorbing bodily fluids;
    two wings extending in the transverse direction from respective longitudinal sides of the primary pad part so as to form a front wing pair, said front wing pair being arranged outside the front end region so that the front end region is not flanked by wings, wherein at least 90% of a top-view-surface of the two wings of the front wing pair is arranged within a subsection of the overall longitudinal extension of the sanitary or incontinence pad, said subsection covering at most one quarter of the overall longitudinal extension of the sanitary or incontinence pad; and
    another two wings extending in the transverse direction from the respective longitudinal sides of the primary pad part so as to form a rear wing pair, wherein at least 90% of a top-view-surface of the another two wings of the rear wing pair is arranged within the rear end region, and wherein the two wings and the another two wings are foldable about a web of an undergarment and are each delimited by a front side flank and a rear side flank, wherein the rear side flank of each of the another two wings of the rear wing pair extend inwardly toward one another so as to form a continuous convex contour which delimits the rear end region of the primary pad part of the sanitary or incontinence pad.

13. A sanitary or incontinence pad, having a longitudinal and a transverse direction, and a front end region in the longitudinal direction which covers at least one quarter of an overall longitudinal extension of the sanitary or incontinence pad, and a rear end region in the longitudinal direction which covers at most one fifth of the overall longitudinal extension of the sanitary or incontinence pad, said sanitary or incontinence pad comprising:
    a primary pad part extending in the longitudinal direction; and having
    an absorption body for absorbing bodily fluids;
    two wings extending in the transverse direction from respective longitudinal sides of the primary pad part so as to form a front wing pair, said front wing pair being arranged outside the front end region so that the front end region is not flanked by wings, wherein at least 90% of a top-view-surface of the two wings of the front wing pair is arranged within a subsection of the overall longitudinal extension of the sanitary or incontinence pad, said subsection covering at most one quarter of the overall longitudinal extension of the sanitary or incontinence pad; and
    another two wings extending in the transverse direction from the respective longitudinal sides of the primary pad part so as to form a rear wing pair, wherein at least 90% of a top-view-surface of the another two wings of the rear wing pair is arranged within the rear end region, and wherein the two wings and the another two wings are foldable about a web of an undergarment and are each delimited by a front side flank and a rear side flank, wherein the two wings of the front wing pair and/or the another two wings of the rear wing pair are folded onto a body-facing topside of the sanitary or incontinence pad by a manufacturer and overlap one another, so that an adhesive coating of the two wings of the front wing pair and/or of the another two wings of the rear wing pair is facing upward, wherein the front wing pair and/or the rear wing pair are provided with a respective flat protective element so that the respective flat protective element covers the adhesive coating of the two wings of the front wing pair and/or respectively of the another two wings of the rear wing pair.

14. The sanitary or incontinence pad of claim 12, wherein the two wings of the front wing pair and/or the another two wings of the rear wing pair extend further than a narrowest point of the sanitary or incontinence pad between the front and rear wing pairs in the transverse direction by 20-70 mm.

15. The sanitary or incontinence pad of claim 12, wherein a top-view-surface of each of the another two wings of the rear wing pair and/or a top-view-surface of each of the two wings of the front wing pair each occupies a portion of 3-7% relative to an overall surface of the sanitary or incontinence pad.

16. The sanitary or incontinence pad of claim 12, wherein a top-view-surface of each of the two wings of the front wing pair is 10-17 $cm^2$, and/or the top view surface of each of the another two wings of the rear wing pair is 10-17 $cm^2$.

17. The sanitary or incontinence pad of claim 12, wherein a predominant portion of each of the front side flanks and rear side flanks encloses on an inside of the respective wings of the front wing pair and/or the rear wing pair an angle of >50° and, up to 85°, with the overall longitudinal direction of the sanitary or incontinence pad.

18. The sanitary or incontinence pad of claim 12, wherein respective flank sections between the front side flank and the rear side flank of each of the two wings and each of the another two wings are shorter than the front and the rear side flanks and extend substantially in the longitudinal direction, and wherein the front side flanks and the rear side flanks transition roundedly into the respective flank sections.

19. The sanitary or incontinence pad of claim 18, wherein a curvature radius in a transition between a longitudinal border of the primary part of the pad, which extends substantially in the longitudinal direction, and the front side flank and/or between the front side flank and the flank section and/or between the flank section and the rear side flank and/or between the rear side flank and the longitudinal border of the primary part of the pad, of a respective wing is 5-12 mm.

20. The sanitary or incontinence pad of claim 12, wherein a predominant portion of the rear side flank of each of the two wings of the front wing pair and a predominant portion of the front side flank of each of the another two wings of the rear wing pair extend in a straight line.

21. The sanitary or incontinence pad of claim 12, wherein the front side flank of each of the two wings of the front wing pair and the rear side flank of each of the another two wings of the rear wing pair extend curved in the shape of an arch.

22. The sanitary or incontinence pad of claim 12, wherein the front side flank of each of the two wings of the front wing pair and the rear side flank of each of the another two wings of the rear wing pair are contoured so as to correspond to one another, thereby enabling alignment of the front-and rear side flanks with one another when folding the sanitary or incontinence pad about an axis which extends in the transverse direction.

23. The sanitary or incontinence pad of claim 12, wherein the front side flank of each of the two wings of the front wing pair and the rear side flank of each of the another two wings of the rear wing pair extend along a circular path or an ellipsis or an oval shape, whose greater main axis coincides with an axis which extends in the transverse direction.

* * * * *